United States Patent [19]

Dürr et al.

[11] Patent Number: 5,026,285
[45] Date of Patent: Jun. 25, 1991

[54] ENOSSAL INDIVIDUAL TOOTH IMPLANT AND LOCKING TOOL FOR USE WITH SUCH AN IMPLANT

[75] Inventors: Walter Dürr, Remchingen; Axel Kirsch, Talstrasse 23, D-7024 Filderstadt, both of Fed. Rep. of Germany

[73] Assignees: Axel Kirsch; Eberle Medizintechnische Elemente GmbH, both of Fed. Rep. of Germany

[21] Appl. No.: 510,861

[22] Filed: Apr. 18, 1990

[30] Foreign Application Priority Data

May 31, 1989 [DE] Fed. Rep. of Germany ....... 3917690

[51] Int. Cl.⁵ .............................................. A61C 8/00
[52] U.S. Cl. ................................. 433/173; 433/201.1; 433/141
[58] Field of Search ............ 433/173, 174, 176, 201.1, 433/141

[56] References Cited

FOREIGN PATENT DOCUMENTS 0164451 7/1987 Japan ................................... 433/174
88/08283 11/1988 PCT Int'l Appl. ................. 433/173

*Primary Examiner*—Gary E. Stone
*Assistant Examiner*—Adriene B. Lepiane
*Attorney, Agent, or Firm*—Hill, Van Santen, Steadman & Simpson

[57] ABSTRACT

An implant for an individual tooth including a metal implant post having a fastening head for receiving the removable denture, the implant post being mounted in a metal spacing element which is threaded in a basic structure that is implantable in the tooth. To hold the spacing element in a fixed, non-twisting and rotatable position, the element is composed of a base portion having a first threaded portion which is received in the basic structure and a second threaded portion of a pitch less than the first portion, which receives a ring element that is threaded thereon and has a shoulder for engaging an upper edge of the basic structure to form a locking arrangement. The invention also is directed to a tool having concentric sleeves which move relative to one another with the inner sleeve having slots for receiving lugs on the base element and the outer sleeve having lugs or projections to be received in the slots on the ring so that the ring can be rotated relative to the base element, which is held by the inner sleeve.

15 Claims, 4 Drawing Sheets

ENOSSAL INDIVIDUAL TOOTH IMPLANT AND LOCKING TOOL FOR USE WITH SUCH AN IMPLANT

BACKGROUND OF THE INVENTION

The present invention is directed to an enossal implant, which is also known as an endosteal or endosseous implant. The implant of the present invention has a basic structure which is implanted in a jaw of the patient and threadably receives a spacer sleeve or element which, in turn, receives a metal implant post having fastening means for receiving an individual tooth, which is a snugly fitting, conditionally removable denture.

U.S. Pat. No. 4,793,808, whose disclosure is incorporated herein by reference thereto and which corresponds to European Published Application 0 216 031, discloses an enossal implant which has proven satisfactory in practice. However, when used as an individual tooth implant, difficulties are encountered in that it is not possible to reliably secure the denture against turning or twisting relative to the base structure unless the individual parts of the implant and the denture are bonded together. Such bonding leads to problems, for example in the case of a subsequent replacement of the denture or when the implant has possible become damaged due to breakage.

SUMMARY OF THE INVENTION

The present invention is directed to providing an enossal individual implant which insures a reliable, simple and, if necessary, detachable securing of a denture against twisting with respect to the basic structure.

To accomplish these goals, the present invention is directed to an improvement in an enossal individual tooth implant which has a metal implant post with a head portion for receiving a removable denture with a snug fit, said implant post being threadably received in the inner bore of a spacer sleeve which, in turn, is threadably received in a bore of a basic structure mounted on a jaw of the patient. The improvements are that a spacer sleeve is formed of a base element or member having threads of a first pitch threadably received in threads of a bore of said basic structure, said base element on an upper end being provided with threads of a second pitch smaller than said first pitch, a ring element or nut-like spacer sleeve top being threadably received on the threads of the second pitch and having a shoulder for engaging an upper annular shoulder or face of said basic structure, upper end faces or surfaces of the base member or element and the ring element being provided with separate tool attachment means for simultaneously securing the base member against twisting as the ring element is rotated relative to the base member, said base member and ring element forming locking means for locking the spacer sleeve in the basic structure against turning and twisting. Thus, after the spacer sleeve base is inserted in the threaded bore of the basic structure, the ring element is rotated relative to the base element to engage the upper annular shoulder and to form a lock-nut arrangement to lock the spacer sleeve in position.

The tool attaching means provided on the end face of the spacer sleeve base can be diametrically directed attachment webs or projections which are received in a groove or slot formed in a tool for holding the base member in an anti-twisting condition. The tool attachment means provided on the end face of the ring element are at least two diametrically facing attachment slots or grooves for receiving a projecting blade of a tool.

In another embodiment of the invention, the inner bore of the base element, which receives the implant post, has a centering thread for attaching a locking tool in the vicinity of its upper edge.

The invention also proposes a locking tool for use with the individual tool implant of the inventive type, which tool has a base wrench complimentary to the tool attaching means provided on the end face of the base element and a second tool arrangement as a top wrench rotatable relative to the base wrench and complimentary to the tool attaching means provided on the end face of the ring element.

According to the invention, it is possible to have centering threads passing through the base wrench and top wrench in a concentric manner for insertion into centering threads of the spacer sleeve base. In the case of a locking tool of the above-mentioned type, the invention optionally proposes that the centering screw is operable by means of a knurled head.

Finally, in the case of a locking tool according to the invention, the base wrench and the top wrench can be provided with fastening levers which extend substantially at right angles to the axis of their relative rotation.

The invention is based o the finding that it is possible to secure or prevent rotation in the case of an individual tooth implant in that the spacer sleeve or element, the so-called insert, which is preferably made of titanium, is constructed in a two-part manner, as described hereinabove. The ring element or nut-like spacer sleeve top engaging on the shoulder or the upper annular edge of the basic structure is rotatable with respect to the spacer sleeve base element and is constructed in a screwable manner with respect to the spacer sleeve base element. As soon as the two-part spacer sleeve has been threaded into the basic structure, there is an easy relative rotation of the ring element with respect to the spacer sleeve bottom or base member, i.e. through an angle of 30°, so that the shoulder of the ring element is pressed with considerable force against the upper edge of the basic structure and the spacer sleeve base is locked by means of said press fit. This leads to a reliable individual tooth implant locking.

Other advantages and features of the invention will be readily apparent from the following description of the preferred embodiments, the drawings and claims.

DESCRIPTION OF THE PREFERRED EMBODIMENTS

Figure 1:
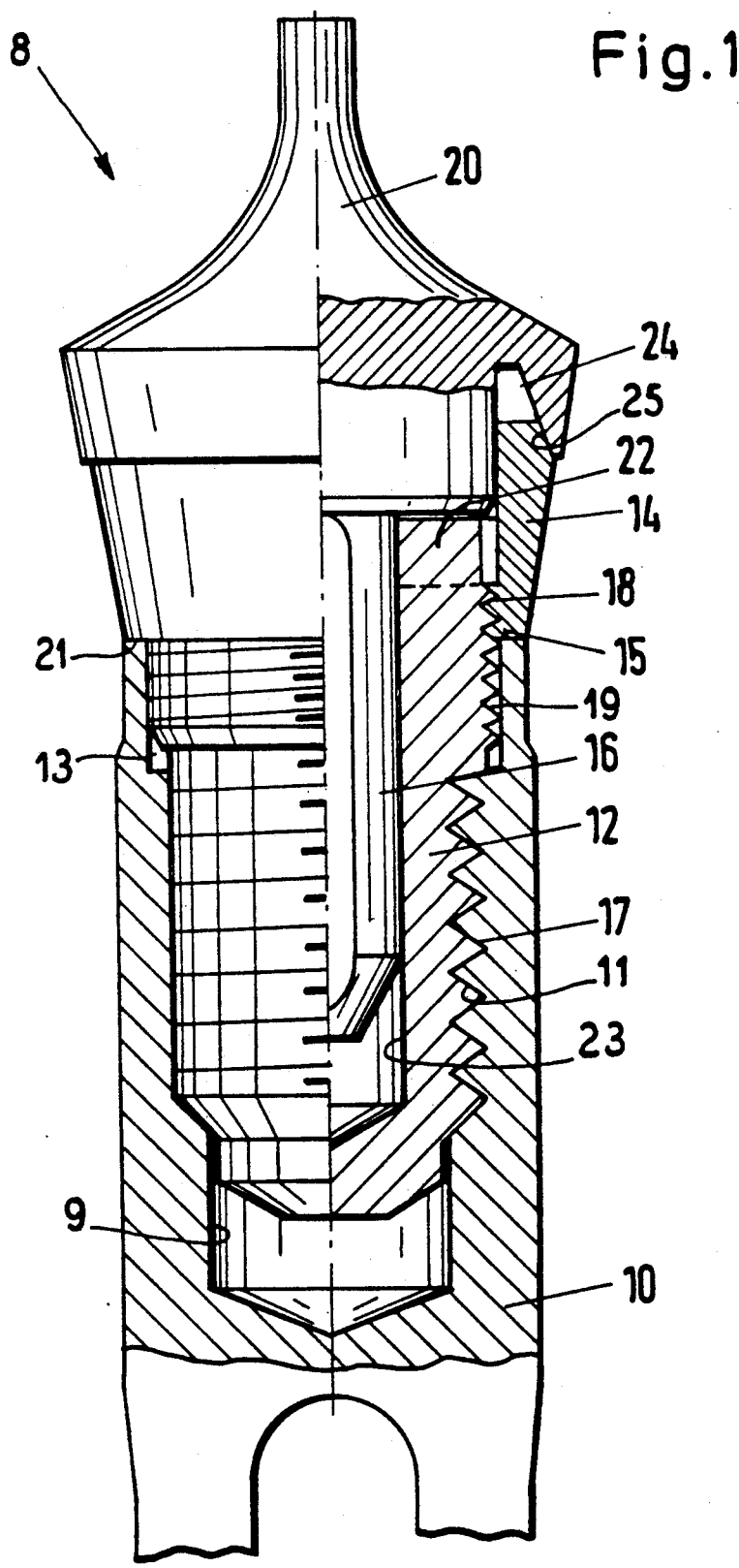
FIG. 1 is a side view of the individual tooth implant with portions broken away to various degrees.

The principles of the present invention are particularly useful when incorporated in a tooth implant, generally indicated at 8 in FIG. 1. The tooth implant 8 has a basic structure 10 of a known type, for example a titanium member coated with hydroxyl apatite. The base structure or member 10 has a bore 9 which has a threaded portion 11 into which is threaded a base element or member 12 of the spacer sleeve. The bore 9 above the threaded portion 11 has a counterbore portion 13 which is free of threads. A spacer sleeve top or ring element 14 is mounted on the base element 12. As illustrated, an upper portion of the base element 12 has threads 17 which coact with the threaded portion 11 to mount the base element in the basic structure 10. Above the threaded portion 17, the base element 12 has a second threaded portion 19 of a pitch which is smaller than the pitch of the portion 17. The top or ring 14 has threads 18 which are threaded onto the threaded portion 19 and has a lower shoulder 21 for engaging a shoulder 15 of the basic structure 10. The spacer sleeve formed by the base element 12 has a bore 23 which receives an implant post 16 of a mounting pin 20 on which the denture is rigidly connected. The mounting pin 20 has an annular groove 25 which receives an upper portion of the ring or top 14.

Figure 3:
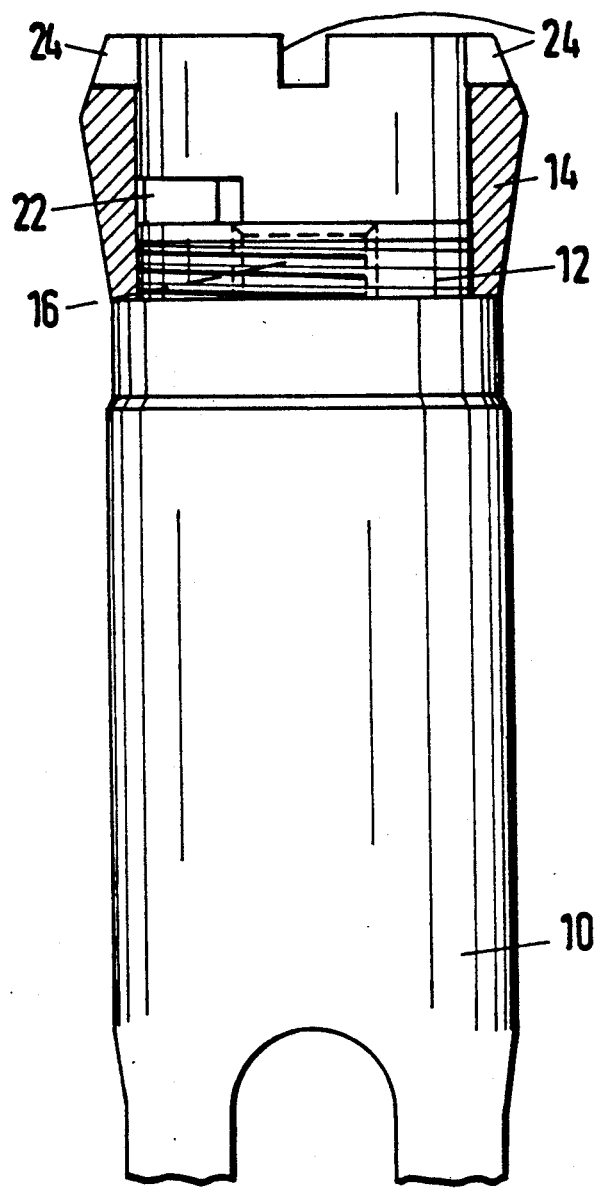
FIG. 3 is a cross sectional view taken along the lines III—III of FIG. 2 with portions in elevation for purposes of illustration.
Figure 2:
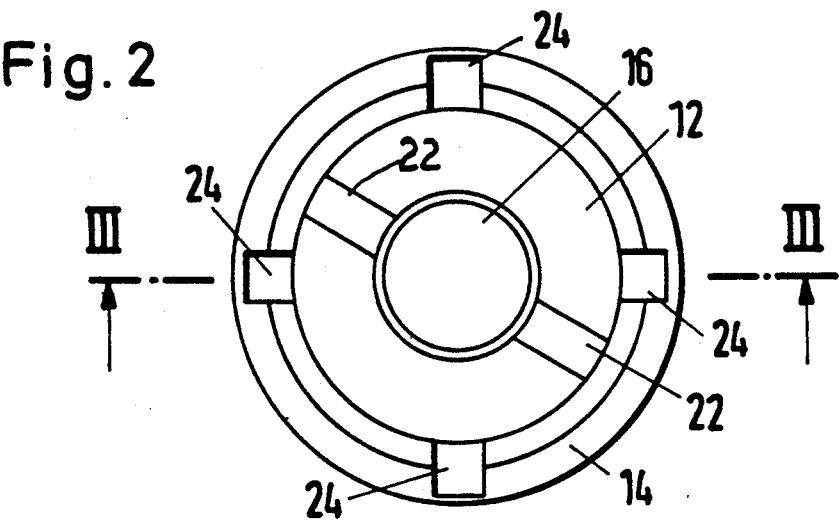
FIG. 2 is a top plan view of the device of FIG. 1 without the implant post.

As illustrated in FIGS. 1, 2 and 3, the spacer sleeve base element 12 is provided with diametrically directed attachment webs or projections 22 which will be received in a slot of a tool to allow rotating of the base element 12 in the basic structure 10. Also, the upper surface of the ring element 14, which is received in the annular groove 25 of the mounting pin 20, is provided with four grooves or slots 24 which are displaced at an angle of 90° with respect to each other and together form a tool attaching means.

Figure 4:
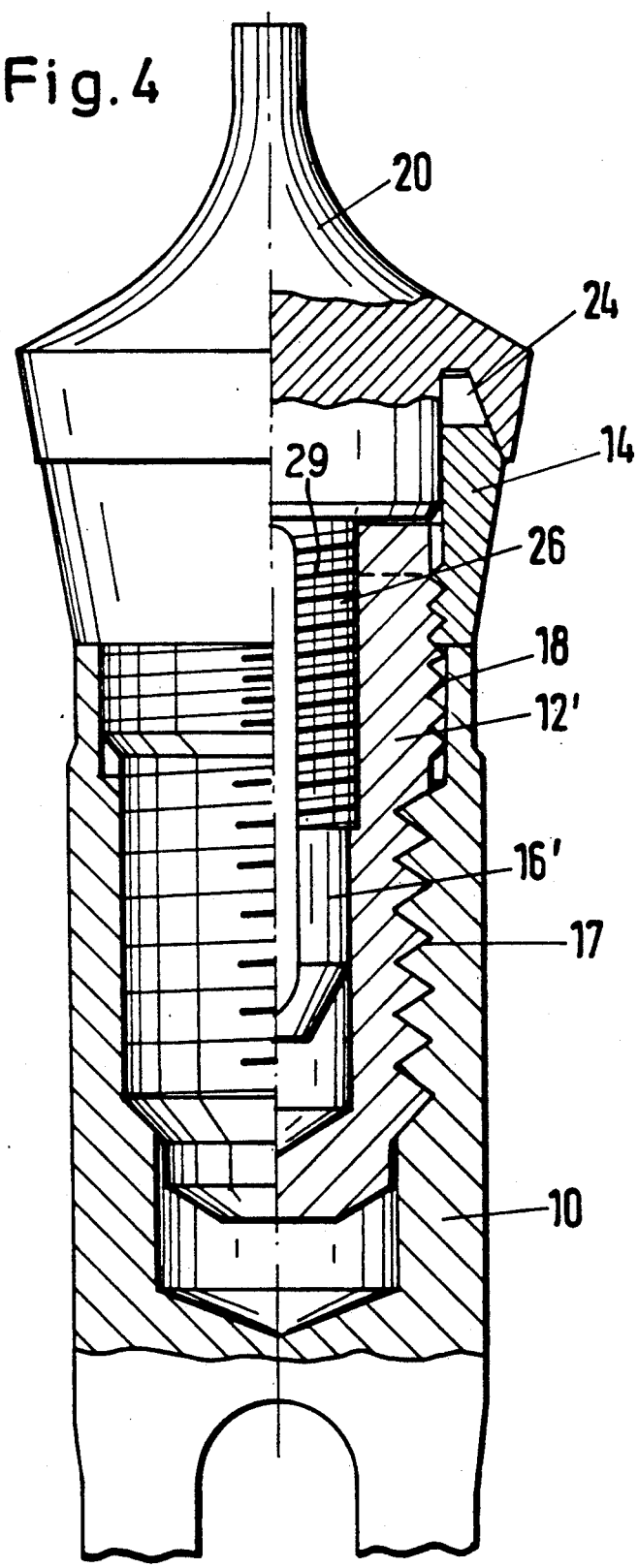
FIG. 4 is a side view with different portions broken away for purposes of illustration of an embodiment of the individual tooth implant in accordance with the present invention.

In the embodiment of the device shown in FIG. 4, the spacer element base 12' has a threaded portion 26 which coacts with a threaded portion 29 of an implant post 16'. The threaded portion 26 provides a centering thread arrangement.

Figure 5:
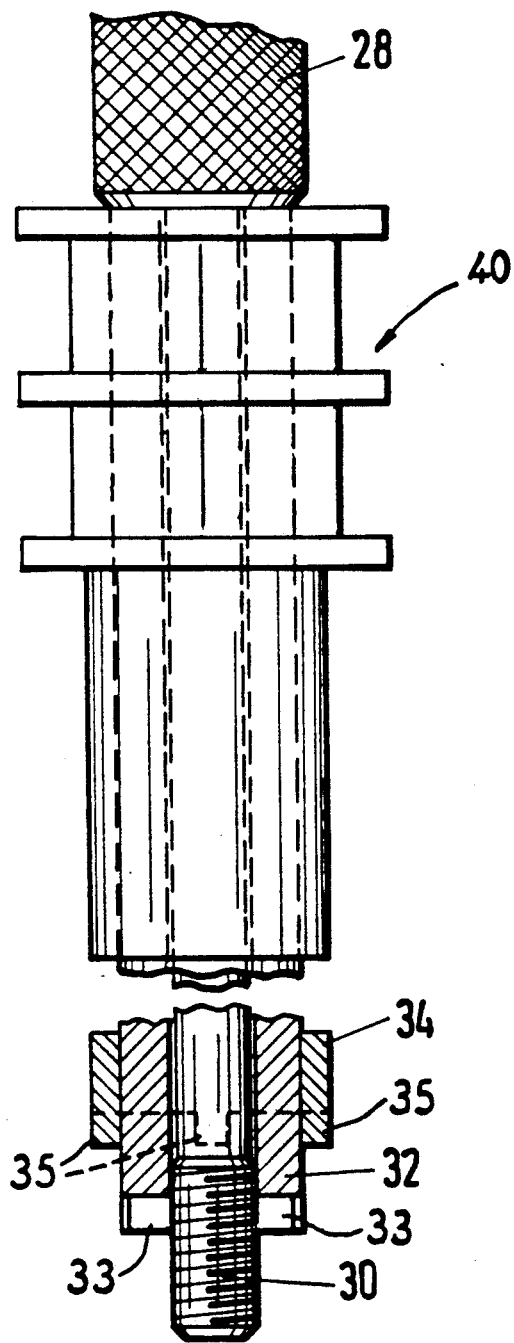
FIG. 5 is a side view of a tool used for inserting the implants of the present invention with portions broken away for purposes of illustration.

In order to lock the base member 12 and its ring 14 in the basic structure 10, a tool, which is generally indicated at 40 in FIG. 5, is provided. The tool 40 has a shaft with centering threads 30 and concentrically arranged on the shaft is a basic wrench 32 in the form of a sleeve which terminates on a lower end with diametrically opposed slots 33, which receive the webs or projections 22 of the base element 12. Concentrically arranged on the sleeve forming the base wrench 32 is a top wrench 34 which is also a sleeve arrangement and has four projections 35 which are spaced apart by 90° around the circumference of the sleeve forming the wrench 34 and are complimentary to the four grooves 24 in the top or ring 14.

When performing an individual tooth implant locking, the following procedure is adopted. First, the ring 14 is assembled on the base element 12 and both parts which are made of titanium are then screwed in a conventional fashion into the basic structure 10. As soon as a shoulder 15 and 21 engage each other, an implant locking or rotation prevention is taken place in the following manner. First, the tool 40 is assembled with the end of the axially extending shaft received in the bore, such as 23, of the base element 12. If the base portion 12' of FIG. 4 is present, then the shaft preferably has the centering threads 30 threaded into the thread 26. In this arrangement, this threading in or positioning will locate the tool so that the grooves 33 of the base wrench 32 receive the web or projections 22 and the top wrench 34 is positioned with its projections 35 received in the grooves 24. By means of small levers, preferably arranged to extend perpendicular to the axis of the shaft and the two wrenches, the base member 12 of the spacer sleeve is secured against rotation, but the top 14 can be turned with respect to the base member or element 12 to an angle of 30° or a half turn. Thus, in a manner due to the different types of threads, the ring element 14 of the spacer sleeve is locked with respect to the base element 12 as the shoulders 15 and 21 are forced into tight engagement with each other.

The construction of the tool attaching means on the spacer sleeve base portion 12 as an attachment web also has the advantage that after locking the base portion 12 and ring 14, the tool can be removed and the implant post 16 can then be inserted, either by a press fit or by screwing into the base element 12' and is engaged with respect to the base portion 12 at a point below the attachment webs 22. In this way, the spacer sleeve can be unscrewed from the basic structure 10, even following a breakage of the implant post 16 so that the individual tooth implant can be repaired without having to remove the basic structure 10 from the jaw.

Although various minor modifications may be suggested by those versed in the art, it should be understood that we wish to embody within the scope of the patent granted hereon all such modifications as reasonably and properly come within the scope of our contribution to the art.

We claim:

1. In an implant for individual teeth having a metal implant post with a head portion for receiving a removable denture with a snug fit, said post being an inner bore of a spacer sleeve, which sleeve is threaded into a bore of a basic structure mounted in the jaw of the patient, the improvements comprising locking means for locking the spacer sleeve in the basic structure against twisting and turning, said locking means including the spacer sleeve having a base element with a first threaded portion with a first pitch threaded in the bore of the basic structure and a second threaded portion adjacent an upper end of the base element of a second pitch smaller than the first pitch and a ring element threadably received on the second portion, said ring element having a shoulder engaging an upper annular face of the basic structure, said ring element on a surface facing away from said shoulder and said base element on an upper end face each being provided with means for attaching a tool to enable simultaneously holding the base element against twisting as the ring element is threaded tightly on the second thread portion of the base element to press the shoulder of the ring element against the upper annular face of the basic structure.

2. In an implant according to claim 1, wherein the inner bore of the spacer sleeve is provided close to its upper end with centering threads for an attachment tool, said inner bore receiving an implant post.

3. In an implant according to claim 1, wherein the means for attaching a tool on the end face of the base element are formed by diametrically opposed upstanding projections adapted to be received in a groove of the tool.

4. In an implant according to claim 3, wherein the means for attaching a tool on the surface of the ring element comprises at least two diametrically facing grooves adapted to receive a blade-like tool.

5. In an implant according to claim 4, wherein the inner bore of the spacer sleeve adjacent the upper end is provided with centering threads for an attachment of a locking tool.

6. In an implant according to claim 3, wherein the inner bore of the spacer sleeve adjacent the upper end are provided with centering threads for attachment of a locking tool.

7. In an implant according to claim 1, wherein the means for attaching a tool on the ring element comprise at least two diametrically facing attachment grooves on the surface of the ring element for receiving a blade-like tool.

8. A locking tool for locking a ring element of a spacer sleeve on a base member inserted in a basic structure, said locking tool comprising a base wrench having means for complimentarily receiving attachment elements on a top of a base member, a top wrench rotatable relative to the base wrench having means complimentary to tool attaching elements provided on an end face of the ring of the spacer sleeve, said base wrench and top wrench being individually rotated relative to one another to enable tightening the ring element on the base element.

9. A locking tool according to claim 8 having an axially extending shaft passing through the base wrench and having an end portion received in a bore of the base member to center the tool as the base wrench and top wrench are inserted in the respective attachment elements.

10. A locking tool according to claim 9, wherein the end portion of said shaft has a centering thread portion for being threadably received in a centering thread of the base member.

11. A locking tool according to claim 10, wherein said shaft on an end opposite the centering thread portion has a knurled head to enable threading the thread portion into said base member.

12. A locking tool according to claim 11, wherein both the base wrench and top wrench are provided with fastening levers extending at right angles to an axis of rotation of said shaft.

13. A locking tool according to claim 10, wherein the base wrench is provided with slots for receiving attachment lugs and the top wrench is provided with space projections for being received in grooves formed in the ring element of the spacer sleeve.

14. A locking tool according to claim 8, wherein the base wrench and the top wrench are both provided with fastening levers extending substantially at right angles to the longitudinal axis of said tool.

15. A locking tool according to claim 8, wherein the attachment elements of the base wrench comprise slots for receiving projections on the base member and the attachment elements on the top wrench comprise space projections for being received in slots provided on the ring element.

* * * * *